United States Patent [19]

Cooper et al.

[11] Patent Number: 5,355,739
[45] Date of Patent: Oct. 18, 1994

[54] APPARATUS FOR MEASURING GAS EMISSION RATE FROM SOIL

[75] Inventors: Charles D. Cooper, Maitland; Debra R. Reinhart, Oviedo; Debra R. H. Seligman, Altamonte Springs, all of Fla.

[73] Assignee: University of Central Florida, Orlando, Fla.

[21] Appl. No.: 37,332

[22] Filed: Mar. 26, 1993

[51] Int. Cl.$^5$ .......................... G01N 7/14; G01N 1/22
[52] U.S. Cl. ..................... 73/864.73; 422/83; 73/19.04; 73/19.05; 73/23.2; 73/863.83; 73/864.34; 73/864.81; 436/25; 436/139
[58] Field of Search ........... 73/864.73, 864.74, 19.04, 73/19.05, 23.2, 864.34, 863.83, 864.81; 422/83; 436/25, 139, 141; 166/250, 254

[56] References Cited

U.S. PATENT DOCUMENTS

| | | | |
|---|---|---|---|
| 1,843,878 | 2/1932 | Laubmeyer | 436/25 |
| 4,026,355 | 5/1977 | Johnson et al. | 166/246 |
| 4,444,041 | 4/1984 | Zison | 73/19 |
| 4,487,054 | 12/1984 | Zison | 73/19 |
| 4,880,973 | 11/1989 | Reynolds | 250/253 |
| 5,063,519 | 11/1991 | Zison et al. | 364/510 |

Primary Examiner—David A. Redding
Attorney, Agent, or Firm—James H. Beusse

[57] ABSTRACT

Gas flux rate from a surface is measured using an elongated tubular housing having a lower open end and an upper open end with a support positioned within the housing a predetermined distance from the lower open end. A gas sampling wand extends into the housing from the upper open end and is supported on the support. The wand has a lower open end at the support generally co-planar with the lower open end of the housing. An air baffle is coupled to the upper open end of the housing for reducing velocity and pressure fluctuations of atmospheric air entering the housing from the upper end. A detector is coupled to the wand for measuring the concentration of selected gases within the housing. A funnel-shaped hood circumscribes the lower open end of the wand and increases the sample collection area of the wand. An air pump is coupled to the wand for drawing air and gases into the wand from the area adjacent the lower open end of the housing. A gas impervious conduit couples the wand to the detector and a flow control valve is coupled to the conduit for controlling the gas flow rate to the detector. A flow meter is coupled in a gas flow path for providing data representative of the volume of gas flowing to the detector. The gas emission rate from the surface is computed using the gas flow rate data and gas concentration data divided by the area encompassed by the housing.

8 Claims, 1 Drawing Sheet

APPARATUS FOR MEASURING GAS EMISSION RATE FROM SOIL

BACKGROUND OF THE INVENTION

The present invention relates to a method and apparatus for measuring gas emission flux from a surface and, in particular, to a method and apparatus for measuring the emission of methane and other organic gases from municipal solid waste landfills.

It has been common practice to bury solid waste products either in municipal solid waste (MSW) landfills or in various government or private hazardous waste landfills. Awareness of the leakage and production of gas emission from such landfills led to the development, under grants from the Environmental Protection Agency (EPA), of a flux chamber for measuring emission rates of various organic gases and vapors from contaminated soil. Since the EPA identifies the flux chamber as a recommended method for estimating baseline emissions from Superfund sites, the flux chamber has become a generally accepted standard. Other methods are known, such as drilling sample wells (U.S. Pat. No. 4,026,355), excavating the surface (U.S. Pat. No. 4,487,054), and measuring soil gas pressures and soil permeabilities (U.S. Pat. No. 5,063,519). A device similar to the flux chamber is shown in U.S. Pat. No. 4,880,973 in an application for sampling radon gas.

The basic flux chamber is described in the *Journal of the Air and Waste Management Assoc.*, Vol. 42, Dec. 1992, pages 1583 et seq. The flux chamber comprises a closed-top chamber with no bottom that is inserted part way into the soil to enclose a defined landfill surface area. A controlled and measured flow of clean, dry sweep air from a compressed air cylinder is introduced into the flux chamber at a rate significantly exceeding the organic gas release rate from the surface. This sweep air mixes with the gaseous emissions from the enclosed landfill surface and transports these gases through an exit port. The total concentration of the methane and other organic gases is measured in the exit air stream directly using a portable gas analyzer. The gas emission rate from the surface is calculated from the measured concentration, the known flow rate of sweep air and the surface area enclosed by the chamber. The emission rate is commonly referred to as a flux rate and is calculated by multiplying the flow rate of sweep air by the measured concentration and dividing the result by the surface area under the chamber. Alternatively, the gas can be captured in a sample container and later analyzed in a laboratory to calculate the emission rate of each species. In cases where the gases in the flux chamber exit stream have been diluted below detection limits, a sample of whole landfill gas can be withdrawn from under the surface for later analysis.

Use of the flux chamber has been restricted by a lack of quality assurance testing, physical difficulties in using the technique, soil disturbances created when inserting the device, extensive time required for testing over large areas, and a tendency to underestimate fluxes due to excessive chamber pressure.

Another significant detriment of the flux chamber method is the need to transport a relatively large chamber to various test sites along with conventional cylinders of clean sweep air and other equipment.

An alternative to flux chamber sampling is a method developed for the California Air Resources Board, called the Integrated Surface Sample (ISS) method. In this method, a person walks a prescribed path holding a hooded sampling wand connected to an instrument that draws a continuous sample of air from near the surface. It is very important to the success of this method that the hooded intake be held exactly a constant distance, typically four inches, from the surface as the person walks.

The ISS method suffers from several operational difficulties, primarily keeping a constant distance. Also, the measured concentrations are highly variable depending on the operator, the shape of the surface and ambient conditions such as the wind. Furthermore, the ISS measurement cannot easily be translated into an emission rate from the surface. Typically, it is used simply to identify compounds being emitted. While the ISS method is faster and easier than the flux chamber method, it is much less accurate and reproducible.

SUMMARY OF THE INVENTION

It is an object of the present invention to provide a method and apparatus which overcomes the above and other disadvantages of the prior art. More particularly, it is an object of the invention to provide a flux measuring method and apparatus which is easily transported, does not require a clean sweep air source, does not disturb the surface being tested, requires less time to complete the measurement, and which can calculate flux rate directly.

In accordance with one form of the invention, there is provided a tubular housing having a lower open end and an upper open end. A support is positioned within the housing a predetermined, fixed distance from the lower open end. A gas sampling wand extends into the housing from the upper open end and rests against the support. Air baffling is positioned over the open upper end of the housing so as to eliminate any differential pressure in the housing attributable to wind velocity. The baffle is pervious to air so as to allow the free flow of air into the housing. The wand is coupled via a conduit to a conventional gas detector which identifies selected species of gas sampled by the wand in the housing. A typical organic gas detected is methane, but others include ethane, butylene, hexane, benzene, and various other organic compounds. A typical housing has a height greater than about twelve inches so that the air entering the upper end is substantially clear of gas emissions from the surface.

An air pump is coupled to the detector for drawing an air and gas mixture into the wand. The end of the wand is hooded to increase its effective collection area and to prevent loss of the organic gases upwards through the tube. The inventors believe there is an optimal hood size which will assure collection of all the gas emissions without interfering with the flow of sweep air so that the concentration range is maintained and the air pressure at the surface is maintained at atmospheric pressure. The detector measures a selected gas concentration, such as a hydrocarbon, and can calculate gas emission flux rate based upon the concentration, the volumetric flow, and the size of the sample area isolated by the tubular housing.

BRIEF DESCRIPTION OF THE DRAWINGS

For a better understanding of the present invention, reference may be had to the following detailed description taken in conjunction with the accompanying drawings in which.

DETAILED DESCRIPTION OF THE INVENTION

Figure 1:
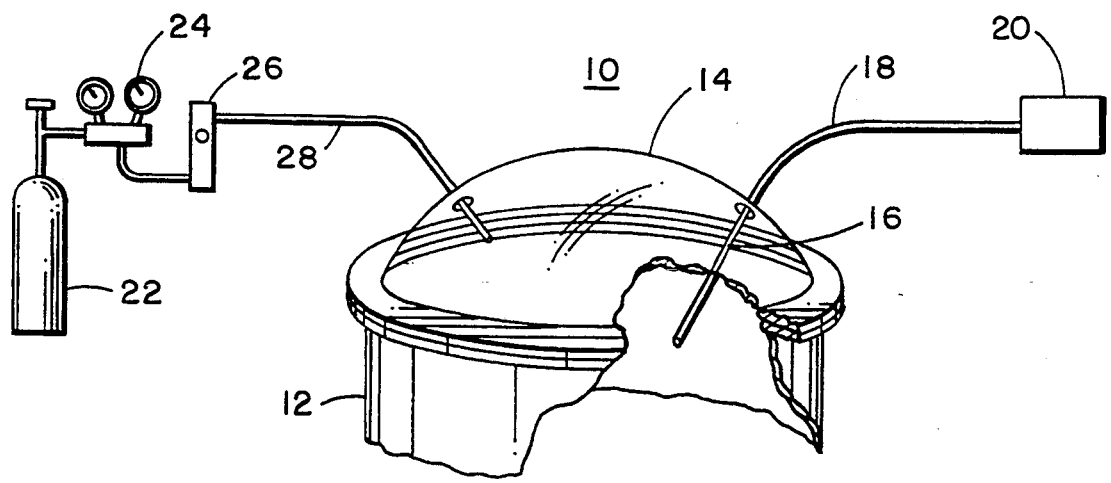
FIG. 1 illustrates a prior art flux chamber arrangement.

Before referring to the present invention, reference is first made to the prior art of FIG. 1 which shows a conventional flux chamber 10 as recommended by the Environmental Protection Agency for estimating surface emissions from landfill sites. The standard flux chamber is essentially a dome superimposed on a cylinder. The shape is selected to provide efficient mixing by eliminating corners and dead spaces. Square or rectangular flux chambers are not recommended due to potentially inadequate mixing of the atmosphere contained within the chamber. The cylindrical skirt 12 of the flux chamber is stainless steel and the dome shaped top 14 may be made of steel or of an acrylic plastic. Preferably, all components in contact with the gas to be analyzed are made of glass, Teflon, or stainless steel. Gas sampling lines associated with the flux chamber are typically Teflon with stainless steel fittings. The flux chamber may be used with a real time gas analyzer or gas emissions from within the chamber may be collected in evacuated stainless steel canisters.

In the illustrated embodiment of FIG. 1, the flux chamber 10 includes the lower cylindrical stainless steel skirt 12 and a dome shaped clear acrylic cover 14. A sampling wand 16 is inserted through the dome shaped cover 14 for sampling gas from within the chamber. A conduit line 18 connects the wand to a real time analyzer 20. The analyzer 20 may be a conventional gas detection instrument such as a flame ionization detector. Such detectors are well known and are commonly used to measure the concentration of volatile organic compounds or VOC's in air. A typical VOC detected from MSW landfill sites is methane. Other types of VOC's are defined within the Florida Statutes §17-2.100 (179) and the definition contained therein is incorporated herein by reference.

The flux chamber 10 is also connected to receive sweep air from a cylinder 22 of clean compressed air or gas. The cylinder 22 has a conventional set of pressure regulating valves 24 which feed the compressed gas through a flow meter 26 at a set pressure and the desired flow rate. The flow rate should be matched to emission rate to keep gas concentration within the range of instrument reading accuracy. A conduit 28 connects the flow meter 26 to the flux chamber 10 such that the air passing through the conduit 28 sweeps the ground surface gases emitted from the surface upward where they can be captured by the wand 16, transported by the outlet line 18, and detected by the analyzer 20.

Use of the above described flux chamber requires both that the flux chamber and the auxiliary equipment be carried to the surface or site to be monitored. Typically, the gas cylinder is large and heavy, the flow meter is bulky, and the flux chamber itself is a relatively large device having a diameter in the neighborhood of about 18 inches. The height of the stainless steel tube may be in the order of seven inches or more. Accordingly, the various pieces of equipment necessary to perform the flux measurements are bulky, cumbersome and difficult to transport. A secondary problem with use of the flux chamber is that a good seal must be maintained around the base of the skirt when it is placed on the surface from which gas emissions are to be measured. It has been common practice to insure such a seal by pressing the chamber down so that the lower edges of the chamber break the upper surface of the ground. While this provides a seal to prevent outside air from sweeping into the chamber and affecting the measurements, the disturbance of the upper surface creates cracks which radiate downward and can greatly affect the measured gas emission rate. In essence, gas which would normally emit from the surface into the flux chamber can flow through the cracks and be diverted outside the chamber. Such an event occurs because the pressure in the chamber is higher due to the external gas flow from the cylinder 22.

Figure 2:
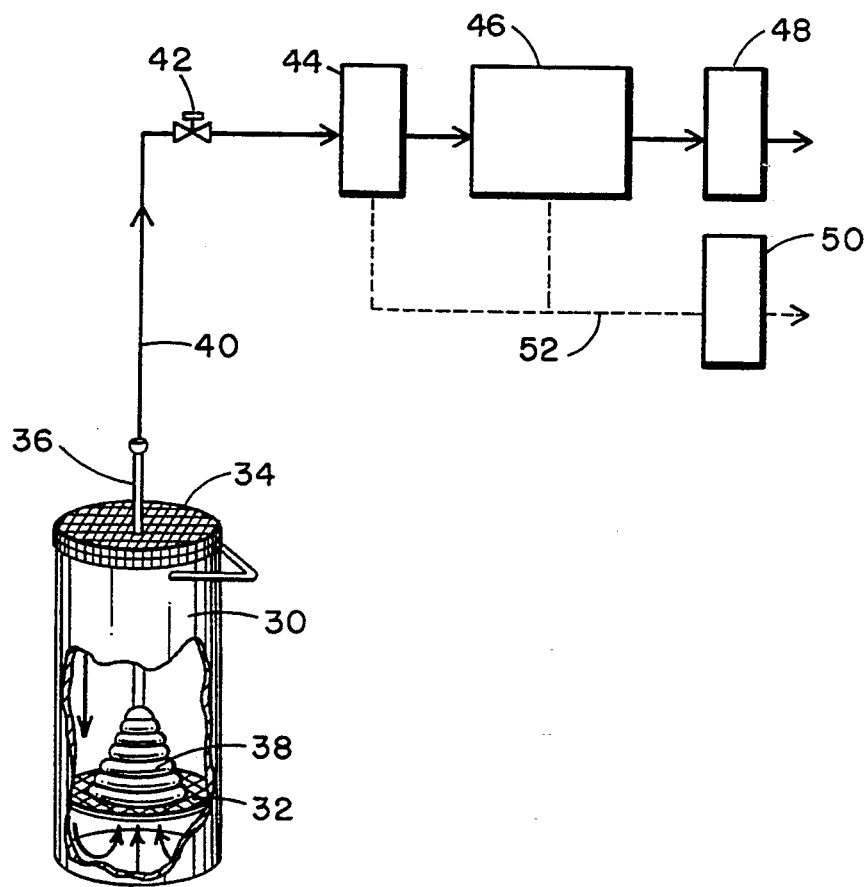
FIG. 2 is a flux tube emission sampling arrangement in accordance with the present invention.

Referring now to FIG. 2, there is shown a gas flux measuring apparatus in accordance with one form of the present invention. The apparatus includes a flux tube or housing 30 having an open lower end and an open upper end. The tube 30 may be a cylindrical tube or pipe and may vary in height from 12 to 36 inches and in diameter from four to 12 inches. In a preferred embodiment, the tube is selected to have a height of 14 inches and a diameter of 6 inches. Within the housing 30 there is positioned a support 32 illustrated as a wire mesh, which is positioned a preselected distance from the open lower end of the housing 30. Preferably, the support 32 is positioned a distance of one inch from the open lower end of the housing 30 for the example in which the housing has an overall height of 14 inches. At the open upper end of the housing 30 there is provided a wind shield cover or baffle 34 which acts to reduce the velocity of air passing into the housing 30 as wind blows across the open upper surface. The function of the baffle 34 is thus to prevent a vacuum effect at the top of the housing 30 as would be caused by the Venturi effect of air blowing across the open upper end and also to prevent air from blowing into the housing if the wind impinges at the open upper end at an angular direction. In essence, the baffle is pervious to air so that there is a free flow of air into the housing 30 with almost no pressure drop, but the air is allowed to flow only into the housing at a rate which matches the rate at which air is extracted for purposes of detection. A measuring wand 36 extends through the open upper end of the housing 30 passing through the baffle 34 and is supported on the grid-like support means 32. The lower open end of the wand 36 preferably is enclosed by a funnel-shaped hood 38 which increases the gas collection area at the end of the wand. Of course, the diameter of the hood 38 at its lowermost end must be less than the inside diameter of the housing 30 in order to allow the air entering the top of the housing 30 to pass around the outside edges of the hood 38 and to sweep the gases from the surface into the hood 38. But the gap between the inside wall of the housing 30 and the hood 38 must not be too great or else some of the gases may escape capture by the hood 38.

The wand 36 is essentially a hollow tube and is connected via a conduit 40 through an adjustable flow control valve 42 and a flow meter 44 to a VOC detector 46. The VOC detector may have an exhaust connected through an air pump 48 which serves to draw the air and gas entering the housing 30 through the conduit into the VOC detector. The sampling wand 36 can be part of a commercially available portable field hydrocarbon gas detection instrument. Such instruments are typically battery-operated and have an internal pump to draw the air samples into the instrument. The air pump 48 represents the internal pump within the instrument.

The gas detection instrument 46 is equipped with an appropriate detector, such as a flame ionization detector, to measure the concentrations of VOC's in the exiting gases. The adjustable flow control valve 42 and flow meter 44 allows the volumetric flow rate of the gas and air mixture taken from housing 30 to be controlled to a predetermined value. This value can then be combined with the VOC concentration factor determined by the VOC detector 46 in a conventional processor 50 to provide an output reading of the gas emission rate from the landfill surface. As indicated by the dotted lines 52, the input signals to the processor 50 may be either automatically taken from the flow meter VOC detector or may be manually input into the processor for calculation purposes. In essence the calculation merely computes the flow rate based on measured concentration from detector 46 and volumetric flow from flow meter 44 and uses this to compute the emission rate. The flux rate then may be calculated directly as a function of the enclosed area. In the illustrated example, the area is simply the open area defined by the open lower end of the housing 30. The measurement of concentration determined by the VOC detector 46 may be referred to as the surface organic vapor (SOV) concentration. By knowing the SOV concentration, the flow rate of air into the detector 46 and the area isolated by the housing 30, the flux rate of the detected organic vapors can be calculated, i.e., flux rate is flow rate (meter 44) multiplied by concentration (instrument 46) divided by surface area defined by tubular housing 30. A background concentration of VOC's may exist in the air entering the top of the housing 30. If the background concentration is anticipated to be greater than a few percent of the measured concentration at the detector 46, then a measurement can be made with wand 36 held above the surface, e.g., pointed upward, to identify background concentration. Since individual measurements of the background concentration are typically highly variable, several measurements may be made to derive an average. Flux rate is then calculated in the manner described by first subtracting the average background concentration from the measured concentration.

The advantages of the above described flux tube arrangement are that it does not require a separate clean air source nor does it require that the surface of the ground or landfill be disturbed in order to assure a positive seal about the open lower end of the housing. Since the dynamic pressure within the housing 30 may be slightly less than ambient due to the air being drawn through the wand 36, and the static pressure is essentially at ambient atmospheric pressure, there is no tendency to force the emissions outside of the housing 30. Furthermore, by drawing air in from the open top end of the housing 30, emissions from adjacent areas outside of the housing 30 are sufficiently diluted by the ambient air so as not to affect the readings taken from within the housing itself. In effect, the arrangement utilizing outside air entering from the top of the housing allows for a limitless supply of relatively clean sweep air.

Table I illustrates the repeatability of test results of SOV measurements taken using the above described flux tube assembly sampling a simulated landfill with a steady methane emission rate. The SOV concentrations for eight samples range from 1200 parts per million to 1350 parts per million methane in air. The mean of the sample concentrations was 1250 ppm with a standard deviation of 65 ppm which is within 5% of the mean value. The table thus illustrates that the measurement of surface organic vapor using the inventive flux tube provides repeatable results.

TABLE I

| Surface Organic Vapor (SOV) Repeatability Test Results | |
|---|---|
| Sample Number | FID Reading, PPM Methane |
| 1 | 1350 |
| 2 | 1250 |
| 3 | 1200 |
| 4 | 1200 |
| 5 | 1250 |
| 6 | 1350 |
| 7 | 1200 |
| 8 | 1200 |

Field measurements at a solid waste landfill taken with applicants' flux tube invention have been compared with field measurements taken using a conventional flux chamber similar to that shown in FIG. 1 and a comparison of the results of the measurements shows a reasonable correlation between the two devices. Accordingly, it is concluded that applicants' flux tube invention as shown in FIG. 2 provides comparable measurements to those obtained using the flux chamber of FIG. 1 but with considerably less difficulty in making the measurements.

While the invention has been described in what is presently considered to be a preferred embodiment, many variations and modifications will become apparent to those skilled in the art. Accordingly, it is intended that the invention not be limited to the specific illustrative embodiment but be interpreted within the full spirit and scope of the appended claims. For example, with a different detector, a radioactive gas such as radon can easily be detected.

What is claimed is:

1. Apparatus for measuring gas flux rate from a surface comprising:
    an elongated tubular housing having a lower open end and an upper open end;
    support means positioned within said housing a predetermined distance from said lower open end;
    a gas sampling wand extending into said housing from said upper open end and supported on said support means, said wand having a lower open end at said support means generally co-planar with said lower open end of said housing;
    air baffling means coupled to said upper open end of said housing for reducing velocity and pressure fluctuations of atmospheric air entering said housing from said upper end; and
    detector means coupled to said wand for measuring the concentration of selected gases within said housing.

2. The apparatus of claim 1 and including a funnel-shaped hood circumscribing said lower open end of said wand for increasing the sample collection area of said wand.

3. The apparatus of claim 1 and including an air pump coupled to said wand for drawing air and gases into said wand from area adjacent said lower open end of said housing.

4. The apparatus of claim 3 wherein said wand comprises a tubular member and including a gas impervious conduit coupling said wand to said detector means and a flow control valve coupled to said conduit for controlling the gas flow rate to said detector means.

5. The apparatus of claim 4 and including a flow meter coupled in a gas flow path between said wand and detector means for providing data representative of the volume of gas flowing to said detector means.

6. The apparatus of claim 5 and including means coupled to said detector means and to said flow meter for determining gas emission rate from the surface using the gas flow rate data and gas concentration data from said detector means.

7. The apparatus of claim 6 wherein said air pump is coupled to an air exhaust port of said detector means.

8. The apparatus of claim 7 wherein said detector means comprises a detector for measuring volatile organic compound concentration in an air-gas mixture.

* * * * *